Figure 1:
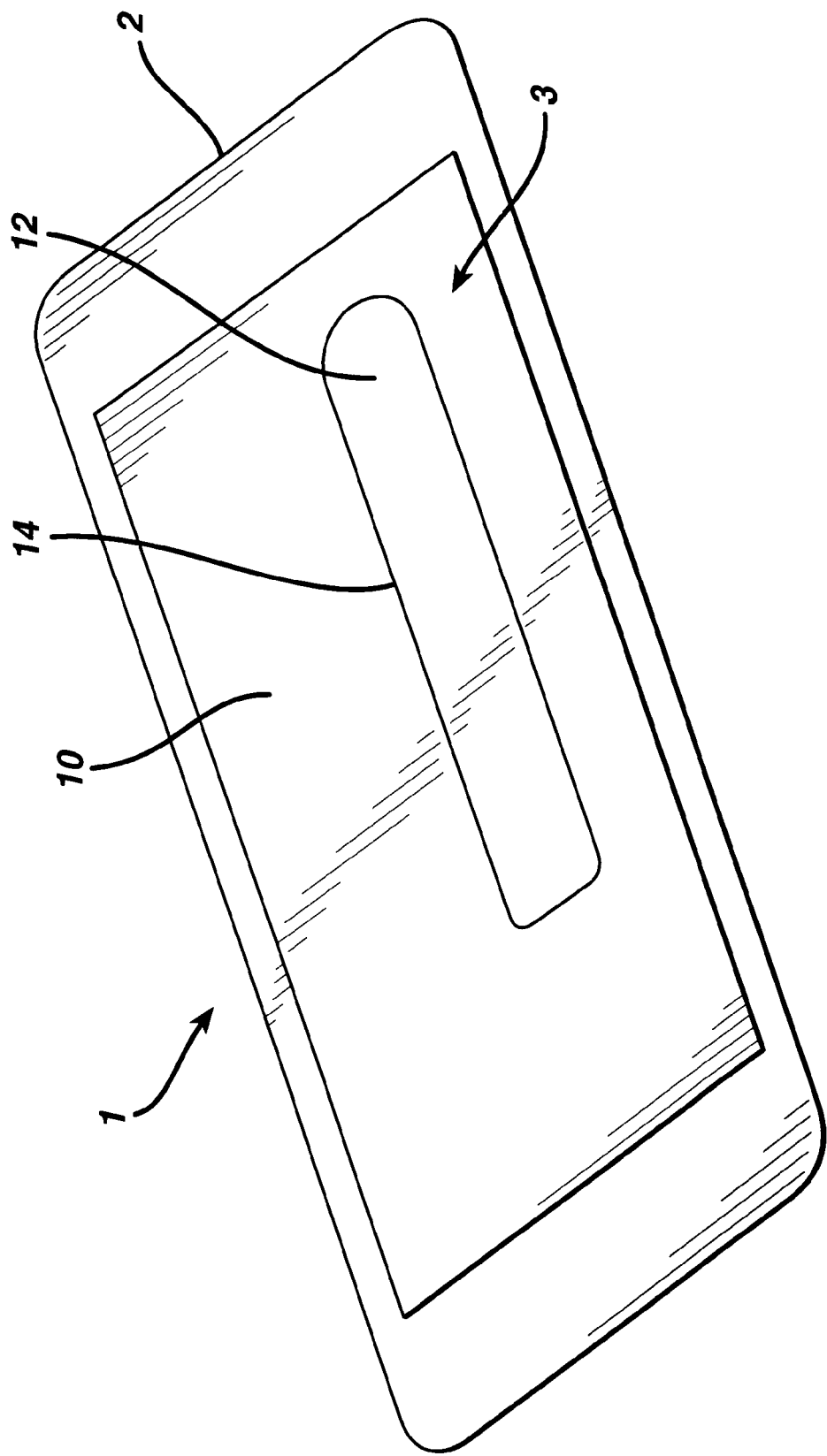

United States Patent [19]
Baumgartner et al.

[11] Patent Number: 5,924,561
[45] Date of Patent: Jul. 20, 1999

[54] PACKAGING FOR SURGICAL SUTURE MATERIAL

[75] Inventors: Karl-Heinz Baumgartner, Wedel; Ulrich Schnoor, Bad Bramstedt, both of Germany

[73] Assignee: Ethicon, Inc., Somerville, N.J.

[21] Appl. No.: 08/885,571

[22] Filed: Jun. 30, 1997

[30] Foreign Application Priority Data

Sep. 24, 1996 [DE] Germany ................ 19641199

[51] Int. Cl.$^6$ .................. A61B 17/06; G09F 3/04
[52] U.S. Cl. .................. 206/63.3; 40/630; 40/674
[58] Field of Search .............. 206/63.3; 40/630, 40/638, 674, 594

[56] References Cited

U.S. PATENT DOCUMENTS

| | | | |
|---|---|---|---|
| 4,585,254 | 4/1986 | Adams | 40/638 |
| 4,910,058 | 3/1990 | Jameson | 40/630 |
| 5,048,678 | 9/1991 | Chambers | 206/63.3 |
| 5,341,922 | 8/1994 | Cerwin et al. | 206/63.3 |
| 5,484,168 | 1/1996 | Chigot | 40/638 |

*Primary Examiner*—Paul T. Sewell
*Assistant Examiner*—J. Mohandesi
*Attorney, Agent, or Firm*—Emil Richard Skula

[57] ABSTRACT

A packaging for surgical suture material has a stuck-on label (3). The label (3) has a main section (10) provided on the back with contact adhesive, and a transfer part (12) which is punched out of the main section (10) and the back of which, likewise provided with contact adhesive, is stuck onto a first protective paper. The edge region of the first protective paper extends beyond the edge (14) of the transfer part (12) and is stuck by means of the contact adhesive to the back of the main section (10). The surface area of the first protective paper is smaller than that of the label (3).

2 Claims, 2 Drawing Sheets

PACKAGING FOR SURGICAL SUTURE MATERIAL

The invention relates to a packaging for surgical suture material according to the preamble of Claim 1.

The label stuck onto such a packaging for surgical suture material contains information about the contents of the packaging.

In order to guarantee appropriate treatment of a patient following an operation, it may be necessary to record accurately the suture material used in the operation. If this takes place during the operation, this occupies staff for a relatively long time, and may lead to incorrect records. Post-operational recording would have to take place from memory, which is particularly prone to errors. Before the operation, it is not yet known precisely which surgical suture material is actually required.

It is therefore the object of the invention to create the possibility of documenting quickly and reliably the surgical suture material used or employed in an operation.

This object is achieved by a packaging for surgical suture material having the features of Claim 1 as well as by the use of a label having the features of Claim 6 for sticking onto a packaging for surgical suture material. Advantageous versions of the invention emerge from the subclaims.

The packaging according to the invention for surgical suture material is provided with a stuck-on label. The label has a main section and a transfer part punched out of the main section. The back of the main section is coated with contact adhesive, as is the back of the transfer part. The back of the transfer part is stuck onto a first protective paper to which the contact adhesive adheres only moderately well so that the transfer part can be peeled off relatively easily. The term "protective paper" is to be understood here in a very wide sense. For example, silicone paper is suitable as protective paper, but a plastic film is also conceivable.

The edge region of the first protective paper extends beyond the edge of the transfer part and is stuck to the contact adhesive on the back of the main section. The surface area of the first protective paper is smaller than that of the label. The effect of this design is that the first protective paper is held securely on the packaging for surgical suture material by the main section, even if the back of the first protective paper itself is not provided with adhesive.

The transfer part can be easily peeled off from the packaging according to the invention for surgical suture material and can be stuck, for example, onto a records sheet containing patient-related data. This can take place quickly and effortlessly during an operation, and it is ensured that the information contained on the transfer part and relating to the surgical suture material is transferred in a correct manner to the records sheet, and is therefore documented. The transfer part is preferably provided on the front with a bar code in which the desired information is encoded.

It is, for example, also conceivable to stick the transfer part onto an order form in order easily to reorder used surgical suture material. The label of the packaging according to the invention for surgical suture material can have several transfer parts in order to transfer the desired information to several different places, e.g. onto a records sheet having patient data and onto an order form.

In a preferred version, in an edge zone of the transfer part, the contact adhesive on the back of the transfer part is covered by a covering. The covering can be punched out of the first protective paper. The result of this is that the back of the transfer part is not sticky in this edge zone and can be peeled off more easily from the first protective paper. The edge zone can be connected via a perforation to the remaining area of the transfer part so that, after the transfer part has been stuck at the desired location, e.g. on a records sheet, the then no longer required edge zone with the non-sticky covering can be easily torn off.

The packaging for surgical suture material preferably contains a sterile inner packaging with surgical suture material, in which, for example, a thread or several threads, optionally with needles fastened thereto, are housed. In this case, therefore, the packaging acts as a surrounding packaging for the inner packaging. In principle, it is also conceivable to store the surgical suture material directly in the packaging according to the invention.

To produce a packaging for surgical suture material, the label meant for sticking on is preferably supplied in a form in which the contact adhesive, which is not covered by the first protective paper, on the back of the main section is covered by a second protective paper, which is to be removed prior to sticking onto the packaging for surgical suture material. Just like the first protective paper, the second protective paper may consist, for example, of silicone paper or a film. The first protective paper is preferably punched out of the second protective paper.

In a preferred version, a number of similar labels are arranged next to one another, e.g. on sheets or in the form of a strip, the respective second protective papers being joined together.

Information can be printed on the label or labels by means of a printer, preferably a laser printer, during the production process for the packagings for surgical suture material. Production and the provision of the desired information can be closely linked in this way, and shortfalls or surpluses of labels are avoided.

The invention is explained in more detail below with reference to an embodiment.

The drawings show in

FIG. 1 a perspective view of a packaging according to the invention for surgical suture material having a stuck-on label and FIG. 2 in part (a) a perspective view of a label prior to sticking onto a packaging for surgical suture material, supplied with a second protective paper, and in part (b) a perspective view of the back of the label after peeling off from the second protective paper, a first protective paper being recognizable.

FIG. 1 shows a packaging for surgical suture material in perspective view from the top. In the embodiment, the packaging 1 has two aluminium foils which are positioned one above the other and are stuck together along their common edge running around the periphery. The outer edge zone of the two foils is not provided with adhesive on the narrow side 2, so that the foils can be easily gripped there at the top side and the bottom side, and the packaging 1 can be torn open. In the inside of the packaging 1 is located a sterile inner packaging with surgical suture material which is not shown in the figures and can be easily removed when the packaging 1 has been opened.

A label 3 is stuck onto the top side of the packaging 1, i.e. onto the upper of the two aluminium foils. The label 3 has a main section 10 and a transfer part 12 which is punched out (completely or partially) of the main section 10 along its edge 14. In the embodiment, the main section 10 and the transfer part 12 consist of paper. The upper aluminium foil of the packaging 1 is advantageously stiffened by the label 3, which eases removal of the inner packaging when the packaging 1 has been torn open.

Figure 2A:
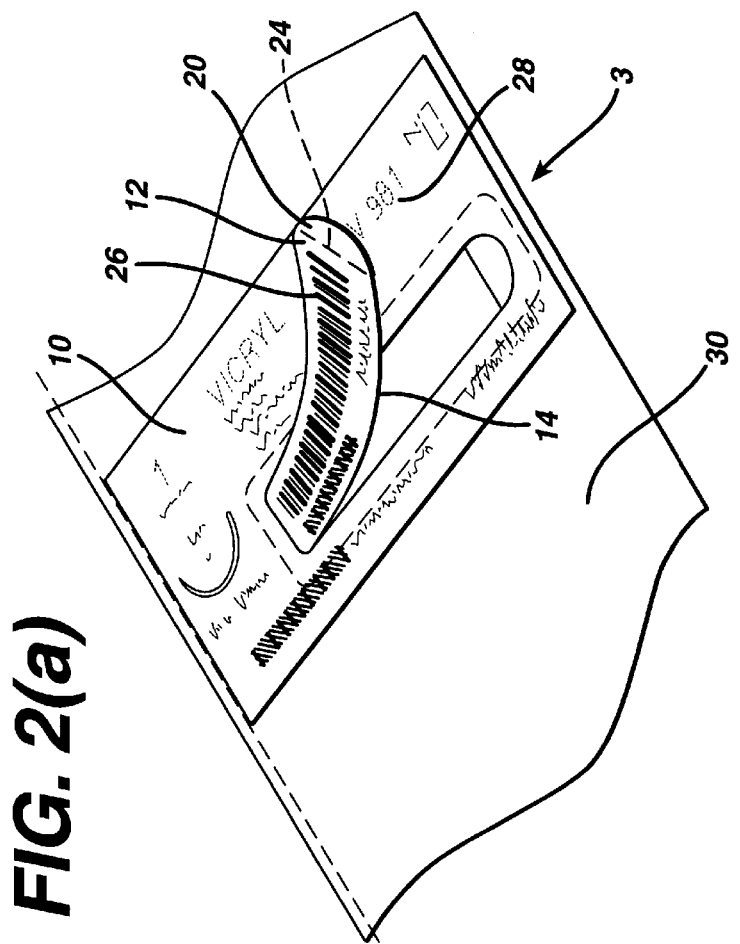
Figure 2B:
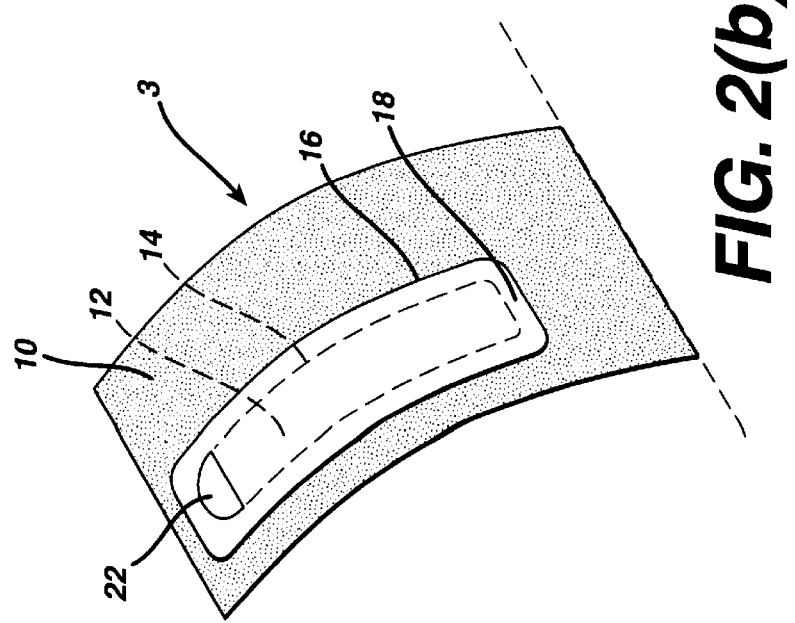

FIG. 2 shows in detail how the label 3 is designed. In FIG. 2(a), the label 3 is located, prior to sticking onto a packaging for surgical suture material, on a protective paper, e.g. a silicone paper or a foil (see below). FIG. 2(b) shows the label 3 from the back, after it has been peeled off from the protective paper mentioned.

The backs of the main section 10 and of the transfer part 12 are coated with a contact adhesive. The contact adhesive of the transfer part 12 is covered by a first protective paper 16, see FIG. 2(b). The surface area of the first protective paper 16 is smaller than that of the label 3, but larger than that of the transfer part 12, so that an edge region 18 of the first protective paper 16 extends beyond the edge 14 of the transfer part 12. The edge region 18 is stuck by means of the contact adhesive to the back of the main section 10. After the label 3 according to FIG. 2(b) has been stuck onto the packaging 1 for surgical suture material, the first protective paper 16 is held securely and firmly on the packaging 1 by the main section 10 although the back of the first protective paper 16 is not coated with adhesive. The transfer part 12 can be easily peeled off from the first protective paper 16, as indicated in FIG. 2(a), because the adhesive force between the contact adhesive on the back of the transfer part 12 and the first protective paper 16 is relatively weak.

In the embodiment, in an edge zone 20 of the transfer part 12, see FIG. 2(a), the contact adhesive on the back of the transfer part 12 is covered by a covering 22, see FIG. 2(b), i.e. the covering 22 is stuck onto the edge zone 20 by means of the contact adhesive. Hence a non-sticky end piece of the transfer part 12 is produced which can be easily gripped and released again, and thereby the removal of the transfer part 12 from the label 3 is made easier. In the embodiment, the covering 22 is punched out of the first protective paper 16. The edge zone 20 is connected to the remaining area of the transfer part 12 via a perforation line 24. After the transfer part 12 has been removed and has been stuck, e.g. onto a records sheet, by means of the contact adhesive on its back, the edge zone 20 with the covering 22 can easily be torn off along the perforation line 24, so that the area of the transfer part 12 remaining on the records sheet is stuck on over its whole surface.

The front of the transfer part 12 carries details about the contents of the packaging for surgical suture material. In the embodiment, this information is encoded in a bar code 26. In addition, an uncoded text statement can also be provided, as is also the case for the inscription 28 of the main section 10, see FIG. 2(a).

As already mentioned, prior to sticking onto the packaging 1, the label 3 is located on a protective paper, here called second protective paper 30, see FIG. 2(a). The second protective paper 30 covers the contact adhesive left by the first protective paper 16 on the back of the main section 10 of the label 3, and hence makes handling of the label 3 easier prior to sticking onto the packaging 1.

The first protective paper 16 is preferably punched out of the second protective paper 30. When producing a label 3, it is possible to carry out the necessary punchings for the transfer part 12, for the first protective paper 16 and also for the covering 22 and the perforation line 24 on the edge zone 20 by punching the label 3 stuck onto the second protective paper 30 from above and from below in one step.

A number of similar labels 3 are preferably arranged next to one another on the second protective paper 30. In this process, sheets or continuous strips, for example, can be formed. Information can be printed on the labels 3 using a printer, preferably a laser printer, during the production process for the packagings for surgical suture material or during the filling of these packagings with surgical suture material, and they can also be provided with a changing batch number. It is then unnecessary to produce labels 3 for stock, and as a result of this, storage and logistics costs fall and it is guaranteed that, on the one hand, there are always enough labels available, but, on the other hand, a surplus of labels is not produced. After imprinting, the labels 3 can be peeled off from the second protective paper 30 by means of a label-dispenser system and stuck onto the packagings for surgical suture material.

We claim:

1. Packaging for surgical suture material, having a stuck-on label (3), wherein the label (3) comprises a main section (10) provided on the back with contact adhesive, and a transfer part (12) which is punched out of the main section (10) and the back of the transfer part (12) is provided with contact adhesive, which is stuck onto a first protective paper (16), the edge region (18) of which extends beyond the edge (14) of the transfer part (12) and is stuck by means of the contact adhesive to the back of the main section (10), the surface of the first protective paper (16) being smaller than that of the label (3) and, wherein in an edge zone (20) of the transfer part (12), the contact adhesive on the back of the transfer part (12) is covered by a covering (22), and wherein the covering (22) is punched out of the first protective paper (16), and wherein the transfer part (12) is provided on the front with at least one of a bar code (26) and an uncoded test and wherein the packaging (1) contains a sterile inner packaging with surgical suture material.

2. Use of a label for sticking onto a packaging for surgical suture material, comprising providing a label having a main section (10) provided on the back with contact adhesive, and a transfer part (12) which is punched out of the main section (10) and the back of the transfer part (12) is provided with contact adhesive, which is stuck onto a first protective paper (16), the edge region (18) of which extends beyond the edge (14) of the transfer part (12) and is stuck by means of the contact adhesive to the back of the main section (10), the surface area of the first protective paper (16) being smaller than that of the label (3), and the contact adhesive not covered by the first protective paper (16) on the back of the main section (10) being covered by a second protective paper (30) to be removed prior to sticking onto a packaging for surgical suture material wherein, in an edge zone (20) of the transfer part (12), the contact adhesive on the back of the transfer part (12) is covered by a covering (22), and wherein the covering (22) is punched out of the first protective paper (16), and wherein a plurality of similar labels (3) are arranged next to one another, the respective second protective papers (30) being continuous, and wherein information is printed on labels (3) by means of a printer, during the production process, for sticking onto the packaging for surgical suture material (1).

* * * * *